United States Patent [19]
Bayers

[11] Patent Number: 5,133,751
[45] Date of Patent: Jul. 28, 1992

[54] INTRAOCULAR LENS

[76] Inventor: Jon Bayers, 1441 Liberty St., Ste. 205, Redding, Calif. 96001

[21] Appl. No.: 702,184

[22] Filed: May 20, 1991

[51] Int. Cl.⁵ .............................................. A61F 2/16
[52] U.S. Cl. .......................................................... 623/6
[58] Field of Search ........................................... 623/6

[56] References Cited
U.S. PATENT DOCUMENTS 4,494,254  1/1985  Lopez ..................................... 623/6
4,808,181  2/1989  Kelman .................................. 623/6

Primary Examiner—Ronald Frinks
Attorney, Agent, or Firm—Bielen, Peterson & Lampe

[57] ABSTRACT

An intraocular lens utilizing an optical portion which is capable of vision correction. The optical portion connects to a flexible body which includes a fissure permitting said flexible body to unravel into to an element having a relatively narrow transverse dimension. The flexible body is also capable of reforming into a substantially unitary element having a relatively large transverse dimension.

6 Claims, 2 Drawing Sheets

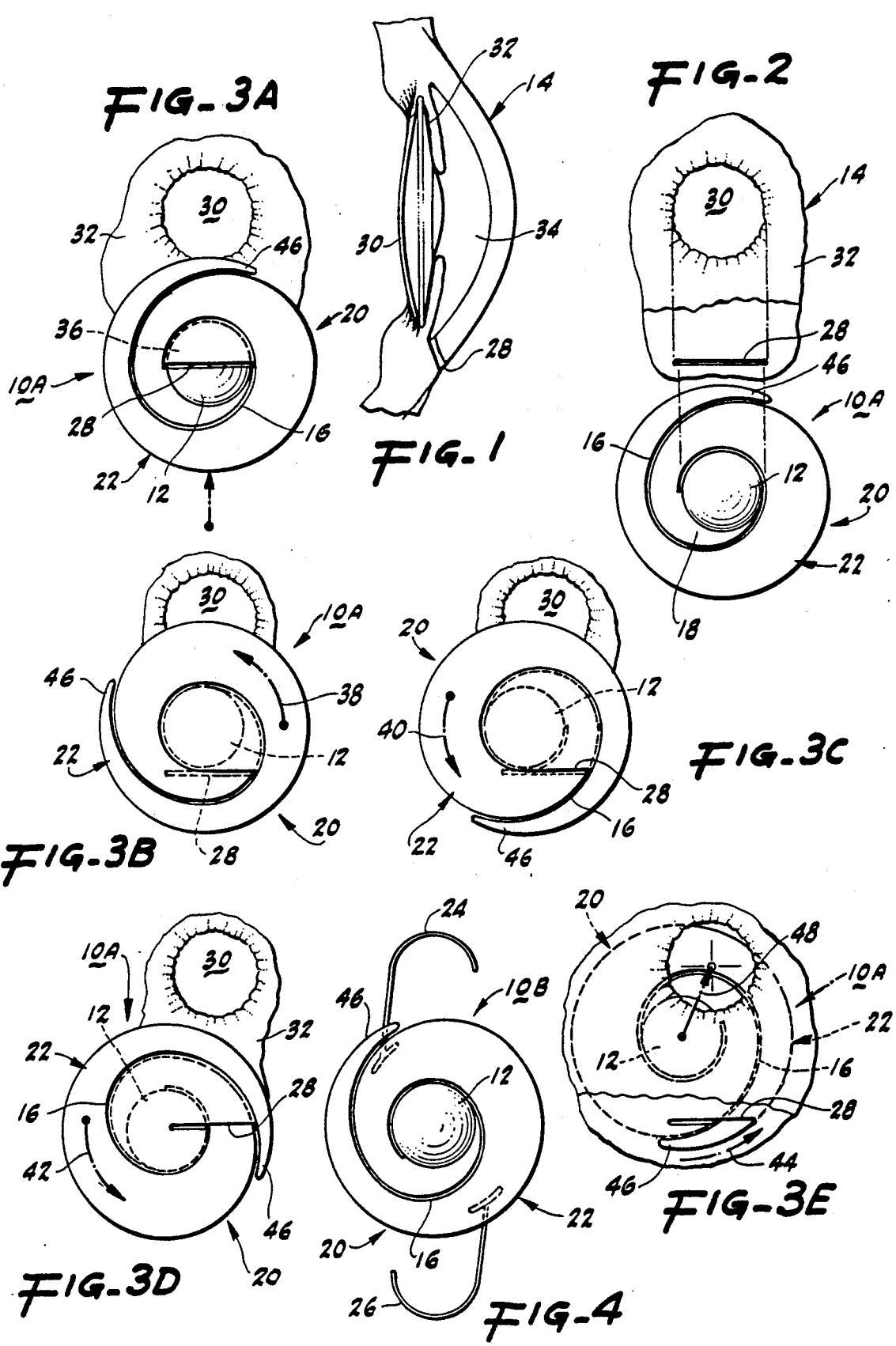

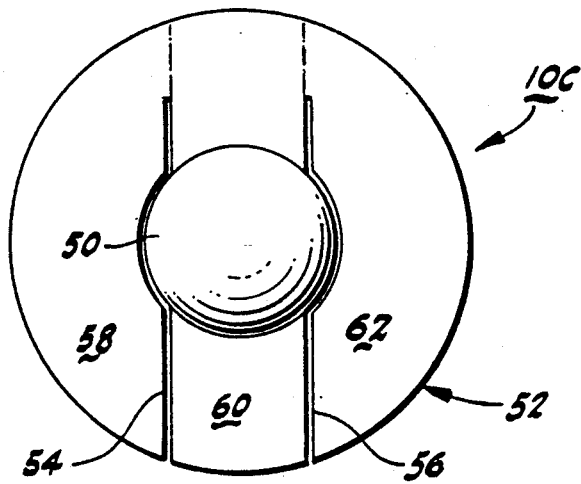
FIG-5
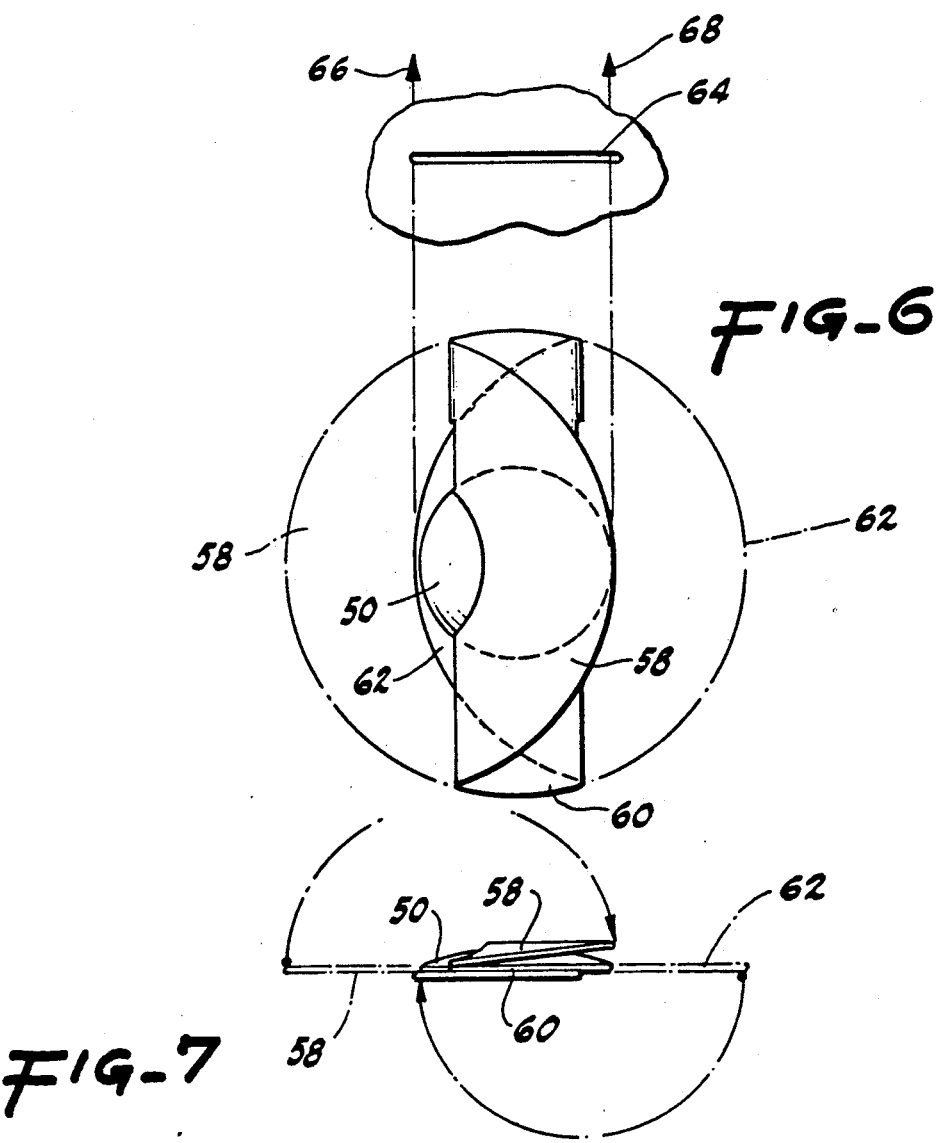
FIG-6
FIG-7

INTRAOCULAR LENS

BACKGROUND OF THE INVENTION

The present invention relates to a novel intraocular lens which is capable of passing through a small surgical incision or wound.

Intraocular lenses have been used to correct cataract conditions for a number of years. Such technique employs the removal of the cataract by known methods. The instrumentation required to remove the cataract requires a rather small (1-2 mm) incision. However, insertion of the intraocular lens, normally into the capsular bag remaining in the posterior chamber of the eye, necessitates a larger incision, about 6 mm. It has been found that smaller incisions minimize any trauma associated with cataract surgery.

In this regard, lenses have been proposed which include a foldable optic portion which may be employed with open or closed loops or haptics. Although foldable lenses reduce the need for a large (6 mm) incision, the instrumentation, in the format a of tube, needed to maintain such lenses in a collapsed configuration greatly cancels the compactness of the foldable lens, requiring a larger than expected wound (4-5 mm). In addition, foldable substances such as silicone material have a relatively low refractive index and, thus, are not perfectly suited for optical corrections. In addition, foldable lenses often become distorted during the folding process and must reform from such stressed configuration to its original shape while inside the eye.

An intraocular lens which is usable with small-incision cataract surgery would be a notable advance in the medical field.

SUMMARY OF THE INVENTION

The present invention relates to a novel intraocular lens which may be employed in small-incision cataract surgery.

The lens of the present invention includes an optical potion which is capable of refracting light. The optical portion may be composed of material which is compatible with eye tissue i.e. silicone and the like. The optical portion may be included in a flexible body which possesses a fissure permitting the flexible body to unravel and reform into a substantially unitary element. The optical portion may be connected to the flexible body or completely integrated into the flexible body such that the entire flexible body possesses light refracting capabilities.

The fissure of the flexible body may curve and take the form of a spiral. Such configuration renders the flexible body as a helical structure which may be tapered from one end to another. Again, the helical body would be capable of unraveling and then reforming into a unitary element capable of being used as an intraocular lens.

In general, the helical body would possess an unraveled transverse dimension which is less than the transverse dimension of the helical body reformed into a substantially unitary element.

In another embodiment of the present invention, the flexible body may include a plurality of fissures which separate the flexible body into at least first and second portions. In this case, the first and second portions would be capable of overlying one another. Where at least three portions are formed by the fissure, such portions, in the form of flaps or wings, would be capable of being interleaved. Thus, this configuration reduces the overall dimension of the flexible body. In this embodiment, the wings would then be unfolded to form a unitary element having a larger, dimension, once the lens is placed in the eye.

In certain embodiments, the present lens would include flexible appendages or haptics to aid in the fixation of the lens in the anterior or posterior chamber of the eye. Such haptics are also flexible such that they maybe folded atop the substantially unitary element formed by the flexible body having an optical portion.

It may be apparent that a novel and useful intraocular lens has been described.

This is therefore an object of the present invention to provide an intraocular lens which may be employed with small-incision cataract surgery without the use of cumbersome tools that require the enlargement of the incision in the eye.

Another object of the present invention is to provide an intraocular lens which may be inserted through a small incision or wound during cataract surgery and includes means for adjusting the size of the optic at the time of insertion.

Yet another object of the present invention is to provide an intraocular lens which utilizes material having a relatively high refractive index and being sufficiently flexible for use in small-incision cataract surgery.

A further object of the present invention is to provide an intraocular lens which is not distorted and stressed during insertion so that its optical characteristics are affected and must return to a prior state by dint of a resilience characteristic.

Another object of the present invention is to provide an intraocular lens having an optical portion integrated into a flexible body which is capable of unraveling and reforming into a unitary element after passage through a relatively small-incision during cataract surgery.

The invention possesses other objects and advantages especially as concerns particular characteristics and features thereof which will become apparent as the specification continues.

BRIEF DESCRIPTION OF THE DRAWINGS

FIG. 1 is an sectional view of the eye depicting the intraocular lens of the present invention in place in the posterior chamber of the eye.

FIG. 2 is a top plan view of the intraocular lens of the present invention formed as a substantially unitary element adjacent incision the eye for insertion of the intraocular lens into the posterior chamber.

FIGS. 3A-E represent a progression of the intraocular lens of the present invention passing through a small incision into the posterior chamber of the eye.

FIG. 4 is a top plan view of an alternate embodiment of the intraocular lens of the present invention utilizing flexible appendages to aide in the positioning of the lens within the eye.

FIG. 5 is a top plan view of yet another embodiment of the intraocular lens of the present invention.

FIG. 6 is a top plan view of the embodiment of the intraocular lens depicted in FIG. 5 with portions interleaved.

FIG. 7 is an end view of the configuration of the intraocular lens depicted in FIG. 6.

For a better understanding of the invention references made to the following detailed description of the preferred embodiments which should be referenced to the prior described drawings.

DESCRIPTION OF THE PREFERRED EMBODIMENTS

Various aspects of the present invention will evolve from the following detailed description of the preferred embodiments which should be taken in conjunction with the prior described drawings.

The invention as a whole is shown in the drawings by reference character 10 and letters distinguish specific embodiments, thereof. With reference to FIG. 2, it may be observed that an intraocular lens 10A is depicted. The intraocular lens 10A includes an optical portion 12 which is capable of correcting vision within an eye 14 FIG. 1. Optical portion 12 may be constructed of any known material which is compatible with eye tissue such as silicone or other polymeric materials. In addition, intraocular lens 10A includes a flexible body 14 which is in the shape of a helix formed along fissure 16. Flexible body 14 connects to optical portion along end 18 thereof. Again, flexible body may be formed of eye compatible material such as silicone. It is also anticipated that the material forming flexible body 14 possess a memory. Shown in FIG. 2, optical portion 12 and connected flexible body 14 form a substantially unitary element 20. It should be understood that although optical portion 12 is depicted as a separate connected member, such optical portion may be formed integrally with flexible body 14 which also may exhibit optical properties. With reference to FIG. 4, flexible body 22 is shown as a disc configuration in which the entire flexible body 22 constitutes an optical portion Intraocular lens 10B of FIG. 4 also includes resilient appendages 24 and 26 which are capable of bending atop or beneath flexible body 22 during the insertion procedure.

Turning again to FIG. 2, it may be observed that flexible body 14 and fissure 16 permit flexible body to unravel or separate to a certain degree. It may be observed from FIG. 2, an incision 28, which may be as small as 2 mm, has been cut into a portion of eye 14 to gain access to capsular bag 30 in the posterior chamber 32 of eye 14. However, it should be noted that intraocular lens 10 may be placed in the anterior chamber 34 of eye 14, FIG. 1. Nevertheless, FIGS. 3A-E depict intraocular lens 10A passing through incision 28 and into the posterior chamber 32 of eye 14. It may be apparent from FIGS. 3A-E, that portion 36 of helical flexible body 14 extends into posterior chamber 32 of eye 14 ab initio. Since fissure 16 permits separation of intraocular lens 10A, the remaining portions of intraocular lens 10A are fed progressively into posterior chamber 32 of eye 14 in a generally curved path according to directional arrows 38, 40, 42, and 44. Although intraocular lens 10A may be visible to the surgeon during this procedure while in the posterior chamber 32, the portions of intraocular lens 10A within chamber 32 are shown in dashed lined configuration. End portion 46 of flexible body 14 passes through incision 28 last. After passage into posterior chamber 32 of eye 14, incision 28 may be closed and sutured. Flexible body 14 is then capable of assuming the configuration depicted in FIG. 1 where a substantially unitary element 20 passes into posterior chamber 32 and overlies capsular bag 30. Such movement is illustrated by directional arrow 48, FIG. 3E.

Turning to FIGS. 5-7, another embodiment 10C of the intraocular lens of the present invention is depicted. Intraocular lens 10C includes an optical portion 50 which again is shown as being separate from a flexible body 52. Again, flexible body 52 includes an optical portion may be a unitary element possessing optical refractive capabilities throughout. With respect to embodiment 10C a pair of fissures 54 and 56 effectively separate flexible body 52 into portions 58, 60, and 62. As was the case with embodiments 10A and 10B, embodiment 10C is composed of material compatible with eye tissue and exhibiting the proper optical qualities. With reference to FIGS. 6 and 7, it may be observed that portions 58 and 62 of flexible body 52 serve as flaps which fold over portion 60 in interleaving fashion. With reference to the embodiments depicted in FIGS. 6 and 7, lens 10C may be inserted through small-incision 64 according to directional arrows, 66 and 68. Incision 64 leads to posterior chamber 32 of eye 14 as illustrated in the progressive insertion FIGS. 3A-E.

In operation, the surgeon effects the proper incision 28 or 64, FIGS. 2 and 6 respectfully, in the eye 14. With respect to the embodiment 10A of intraocular lens of the present invention the surgeon then forces first end portion 36 of flexible body 14 through incision 28 until end portion 46 passes through the same. Flexible body 14 including optical portion 12 then forms a substantially unitary element 20 found in FIG. 2. Subsequently, element 20 is positioned over capsular bag 30 of eye 14. With respect to embodiment 10B, appendages 24 and 26 are bent over flexible body 22 and inserted in the same manner as shown in FIGS. 3A-E. After passage of embodiment 10B into eye 14, appendages 24 and 26 spring outwardly to aid in the fixation of intraocular lens 10B. Embodiment 10C is passed through incision 64, FIGS. 6 and 7, after folding of portions 58 and 62 upon one another (directional arrows 66 and 68). After passage into eye 14 through incision 64, embodiment 10C is unfolded into a substantially 10 unitary body 70 depicted in FIG. 5.

While in the foregoing, embodiments of the invention have been set forth in considerable detail for the purposes of making a complete disclosure of the invention, it may be apparent to those of skill in the art that numerous changes may be made in such details without departing from the spirit and principles of the invention.

What is claimed is:

1. An intraocular lens comprising;
   a. an optical portion;
   b. a flexible body, said flexible body including a fissure permitting said flexible body to separate and to reform into a substantially unitary element, said optical portion being included as at least a part of said flexible body, said flexible body including said optical portion having the configuration of a helical body, the transverse dimension of said unraveled helical body being no greater than said transverse dimension of said helical body reformed into a substantially unitary element.

2. The intraocular lens of claim 1 in which said fissure is of a substantially spiral configuration.

3. The intraocular lens of claim 1 which additionally comprises at least one appendage linked to said flexible body and extending outwardly therefrom.

4. The intraocular lens of claim 1 in which said fissure separates said flexible body into at least a first and second portion and said first portion is capable of overlying said second portion.

5. The intraocular lens of claim 1 in which said helical body is tapered from relatively wide first end portion to a relatively narrow second end portion.

6. The intraocular lens of claim 1 which further comprises at least one flexible appendage linked to said flexible body said flexible appendage being capable of overlying said flexible body and included optical portion.

* * * * *